(12) United States Patent
Yang et al.

(10) Patent No.: US 11,116,993 B2
(45) Date of Patent: Sep. 14, 2021

(54) CATHETER APPARATUS AND BRACHYTHERAPY SYSTEM

(71) Applicant: BRAXX BIOTECH CO., LTD, Taipei (TW)

(72) Inventors: Kai-Lin Yang, Taipei (TW); Hsuan-Mien Wang, Taipei (TW); Wei-Jer Chang, New Taipei (TW)

(73) Assignee: BRAXX BIOTECH CO., LTD, Taipei (TW)

( * ) Notice: Subject to any disclaimer, the term of this patent is extended or adjusted under 35 U.S.C. 154(b) by 431 days.

(21) Appl. No.: 16/305,048

(22) PCT Filed: Jun. 17, 2016

(86) PCT No.: PCT/CN2016/086112
§ 371 (c)(1),
(2) Date: Nov. 27, 2018

(87) PCT Pub. No.: WO2017/214956
PCT Pub. Date: Dec. 21, 2017

(65) Prior Publication Data
US 2020/0316402 A1 Oct. 8, 2020

(51) Int. Cl.
*A61N 5/10* (2006.01)
*A61M 25/10* (2013.01)
(Continued)

(52) U.S. Cl.
CPC .............. *A61N 5/1007* (2013.01); *A61B 6/12* (2013.01); *A61B 6/425* (2013.01);
(Continued)

(58) Field of Classification Search
CPC ...... A61N 5/1001–1002; A61N 5/1007; A61N 5/1027; A61N 2005/1003;
(Continued)

(56) References Cited

U.S. PATENT DOCUMENTS 5,910,101 A 6/1999 Andrews et al.
5,976,106 A * 11/1999 Verin .................... A61N 5/1002
604/103.07
(Continued)

FOREIGN PATENT DOCUMENTS

CN 202387089 U 8/2012
WO 2015153595 A1 10/2015

OTHER PUBLICATIONS

Hitoshi Ikushima, Radiation therapy: state of the art and the future, The Journal of Medical Investigation, Feb. 2010, pp. 1-11, vol. 57.
International Search Report of PCT Patent Application No. PCT/CN2016/086112 dated Feb. 24, 2017.

*Primary Examiner* — Thaddeus B Cox (57) ABSTRACT

A catheter apparatus (10) includes a tubular member (11); multiple fluid-flow pipe members (13), each having a proximal end (19) and a distal end (18), and being disposed along a first axial direction of the tubular member; multiple node members (15) disposed along a first axial direction of the tubular member, wherein two adjacent node members (15) form a segment (1a); and a periphery member (14), wherein the periphery member (14) wraps the multiple node members (15) to form a space (1b) with the segment (1a) formed between the two adjacent node members (15). The catheter apparatus (10) can irradiate the entire diffuse tumor during one brachytherapy process without repeated placement of the catheter. Meanwhile, it can be smoothly inserted into the patient's narrow body cavity because there are no external balloons. A brachytherapy system adopts the catheter apparatus (10).

11 Claims, 7 Drawing Sheets

(51) Int. Cl.
*A61B 6/12* (2006.01)
*A61B 6/00* (2006.01)

(52) U.S. Cl.
CPC .... *A61M 25/1011* (2013.01); *A61M 25/1018* (2013.01); *A61N 5/1014* (2013.01); *A61N 5/1039* (2013.01); A61M 2025/1015 (2013.01); A61N 2005/1008 (2013.01); A61N 2005/1021 (2013.01)

(58) Field of Classification Search
CPC .... A61N 2005/1008; A61N 2005/1018–1025; A61M 25/1006; A61M 25/1009; A61M 25/1011; A61M 25/1018; A61M 2025/1013; A61M 2025/1061
See application file for complete search history.

(56) References Cited

U.S. PATENT DOCUMENTS

| | | | |
|---|---|---|---|
| 6,258,019 B1 * | 7/2001 | Verin | A61M 25/10 600/1 |
| 6,416,457 B1 * | 7/2002 | Urick | A61N 5/1002 600/3 |
| 6,527,692 B1 | 3/2003 | Weinberger | |
| 6,575,932 B1 | 6/2003 | O'Brien et al. | |
| 7,384,411 B1 | 6/2008 | Condado | |
| 2011/0257459 A1 * | 10/2011 | Sutton | A61M 37/0069 600/7 |
| 2012/0172651 A1 * | 7/2012 | Cutrer | A61N 5/1015 600/4 |
| 2017/0173362 A1 * | 6/2017 | Lamoureux | A61N 5/1007 |

* cited by examiner

CATHETER APPARATUS AND BRACHYTHERAPY SYSTEM

TECHNICAL FIELD

The present application relates to a catheter apparatus for use in brachytherapy, particularly a catheter apparatus and a brachytherapy system with inflatable and deflatable members.

BACKGROUND

Radiation therapy techniques are divided into two categories, namely, teletherapy and brachytherapy. Brachytherapy for the tumor is by inserting a catheter into a body cavity or an organ, placing the catheter close to the surroundings of the tumor tissue, then transporting the radioactive source into the catheter with the after-loading brachytherapy instrument, so that the radiation emitted by the radioactive source is closely irradiated to the tumor area. The high-energy radiation, transferred in the form of light wave or high-speed particle, will destroy the tumor cells. Brachytherapy is a technique for inhibiting tumor cells growth. Brachytherapy is particularly suitable for treating tumors grown in a body cavity, such as esophageal cancer, cervical cancer, endometrial cancer, nasopharyngeal cancer, lung cancer, rectal cancer and other tumors grown in a cavity wherever a catheter can be inserted. In addition, the brachytherapy can also be used for non-luminal tumors by tissue insertion, such as prostate cancer, breast cancer, malignant sarcoma, and brain tumor.

When carrying out teletherapy or brachytherapy, normal tissues around the tumor are affected by the side effect caused by the radiation. Taking the skin as an example, body parts which are rubbed frequently such as armpit and groin, etc. are prone to inflammation and scratch after radiation. Abdominal radiotherapy often causes diarrhea as a side effect. Radiotherapy for head and neck may result in symptoms such as thicken saliva, saliva reduction, altered taste, redness and swelling of the oral mucosa, dry mouth, difficulty and pain in swallowing, and even loss of appetite. Thoracic radiotherapy may cause radiation pneumonitis, inflammation of the esophagus, and even acute bleeding in the esophagus. Therefore, the most ideal condition for radiation therapy is to administer a dose sufficient to cause the death of tumor cells while protecting normal tissues.

Figure 1:
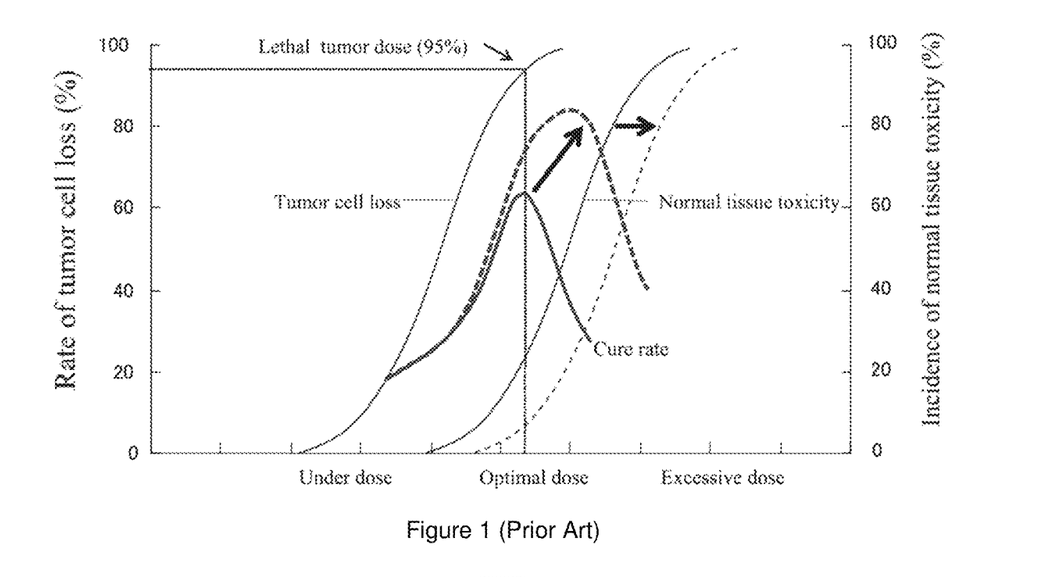
FIG. 1 shows the relationship between radiotherapy dose and tissue toxicity.
Figure 2:
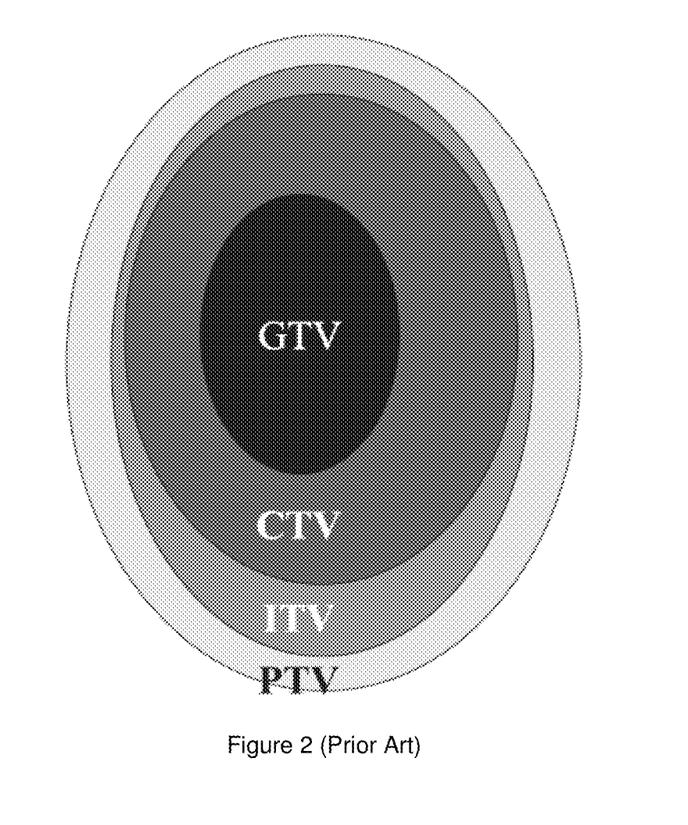
FIG. 2 is a schematic of the radiation area and deviation of displacement of teletherapy.

The side effect of radiation therapy is related to the area exposed to the radiation and radiation dose. Taking brachytherapy as an example, the closer to the radioactive source the normal tissues are, the higher dose they receive, and the greater the side effect is. Since the radioactivity is inversely proportional to the square of the distance from the radioactive source, the optimal dose is the one which causes the death of tumor cells but does not harm the normal tissues. As shown in FIG. 1 (Hitoshi Ikushima, Radiation therapy: state of the art and the future, The Journal of Medical Investigation Vol. 57 February 2010), a dose for tumor treatment can be escalated by improving dose conformity and dose homogeneity, while reducing the radiation dose and area of the normal tissues (causing the sigmoid curve for normal tissue toxicity to shift to the right), thereby improving the cure rate and reducing normal tissue toxicity. Because of the difference in each patient's body cavity/organ and tumor size, the biggest challenge in clinical personalized medicine is providing the optimal therapeutic dose according to the normal tissues and tumor of each patient and the radioactive source. In addition, the natural internal movement of human organs occurs with the breathing. For example, when inhaling, the diaphragm is lowered and the thoracic cavity is expanded. All organs located in the thoracic cavity will move due to the breathing, resulting in inaccurate radiotherapy. Therefore, the deviation of displacement should be considered during treatment. In FIG. 2 (Hitoshi Ikushima, Radiation therapy: state of the art and the future, The Journal of Medical Investigation Vol. 57 February 2010), gross tumor volume (GTV) is the tumor volume and position on imaging. Clinical target volume (CTV) is the possible range of metastasis. Internal target volume (ITV) is the deviation including internal displacement. Planning target volume (PTV) is the set-up margin of radiotherapy. Since it is impossible to accurately fix the radioactive source relative to the tumor during teletherapy or other brachytherapy by external fixation, other normal tissue will be exposed to radiation dose (ITV and PTV areas). On the other hand, there are several treatments in a brachytherapy. It requires precise positioning to ensure that consistent radiation doses are received by the tumor in each treatment, maintaining consistency and reproducibility of the treatments.

In order for the radiation dose to be relatively uniformly distributed in the affected area and to avoid side effects, development in the catheter results in increased tube diameter for placing the radioactive source in the middle of it. The distance between the surrounding tissues and the radioactive source will be the same after placing the thicken catheter into the body cavity. For instance, the Bonvoisin-Gerard Esophageal Applicator product by Elekta keeps the body cavity open for the convenience of radioactive source delivery by thickening the whole section of the catheter. However, while the whole thicken section has centralized the radioactive source, the shapes of the tumors are different and the sizes of tumor growth differ by different sections. Even the whole catheter section is thickened by the same extent, since the dose of the radioactive source is inversely proportional to the square of the distance, more normal tissue areas will be irradiated and resulted in side effects when a part of the tumor growth is restricted to the superficial area. Meanwhile, at the place where the tumor is relatively large and the stenosis is severe, expansion by the same size may cause the catheter wall to rub against the narrow esophageal wall with tumor, thereby causing bleeding and discomfort of the patient. Furthermore, since the esophagus is a smooth and peristaltic organ, the use of catheter with the entire section thickened and without undulation will easily result in slippery of the catheter with poor fixation.

Figure 3:
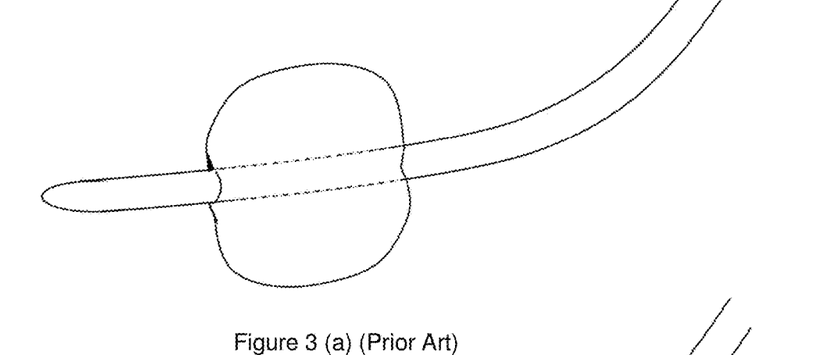
FIG. 3(a) is an illustrative diagram showing the balloon of a current catheter after inflation.
FIG. 3(b) is an illustrative diagram showing the balloon of a current catheter before inflation.

Another catheter by Elekta, Standard Nasopharyngeal Applicator Set, is for inserting into a patient's body cavity and inflating with balloons to keep the cavity open, as shown in FIG. 3(a). However, the balloons are in a state of shrinkage before being inflated, as shown in FIG. 3(b); and may rub against the body cavity wall when entering the body cavity, and cause discomfort to the patient or even damage to the cavity wall.

Taking another catheter disclosed in U.S. Pat. No. 6,575,932B1 as an example, the catheter has two balloons that can be inflated separately, for the convenience of fixation in the body cavity. The distance between two balloons is determined by an intermediate tube between the two balloons, and there is an opening on the intermediate tube for drug administration. However, when this catheter is used for brachytherapy, the intermediate tube allows the radioactive source to pass through; if the distance between the two balloons is too short, the radioactive source will only be suitable for remaining in this small section to ensure that the source is centered and the dose is uniform. It is necessary to place the catheter and radioactive source repeatedly when there is a diffuse tumor which length is above 3 cm in the cavity. That will cause the injury of the cavity easily, and multiple operations are time consuming and exhausting to the patient. In addition, it is quite difficult to combine the segmented doses together. Overdosing caused by overlapping doses at the intersection of two adjacent irradiation areas will easily happen, which may cause unrepaired damage and increase unnecessary risks. If the intermediate distance between the two balloons is elongated, it is difficult to fix the position of the entire tumor. The catheter will likely slip and the position of the radioactive source will likely change because of the patient's breathing or movement. This results in an insufficient therapeutic dose for the tumor cells, while the normal tissue receives an excessive dose which causes injury.

The design of the catheter disclosed in Chinese Patent Publication No. 202387089U attempts to fix the tumor which length is above 3 cm. The catheter has a catheter body, an imaging ring, at least two balloons, a balloon lumen, a balloon filling channel, a balloon injection port, a guide wire channel, and a guide wire channel port. The numbers of balloon injection port, balloon filling channel and balloons are the same. The balloons are in the same diameter and in a long cylindrical shape. During treatment, the end balloon is inflated first, and then the adjacent balloon is inflated in turns; thereby on the basis of the end balloon expansion, the entire length of the balloon can be directly extended without changing the balloon catheter, so as to achieve fixation of the tumor which length is above 3 cm. However, it is much more troublesome during operation due to the necessity of the guide wire. Moreover, the balloons are additional long cylindrical balloons. If the inflation is insufficient, or the adhesion of the balloon on the catheter is offset, the balloon may not be uniformly expanded. As a result, the radioactive source cannot be maintained in the center of the catheter, which will reduce the reproducibility of the treatment plan.

Among the operational difficulties, the treatment of esophageal cancer will most likely cause discomfort to the patient. Attention must be paid to the clinical use of brachytherapy in esophageal cancer treatment, which may cause side effects such as acute bleeding due to the introduction of high radiation doses. Nasogastric tube is usually used for current clinical treatment. However, because of its small diameter, poor fixation, the inability to keep the radioactive source in the center of tube, the nasogastric tube will attach to the esophageal wall randomly, causing the radioactive source to be too close to the normal esophageal wall thereby resulting in excessive dose and formation of radiation hotspots, which will easily cause serious side effects. This affects the doctors' willingness to use nasogastric tube. To prevent the serious side effects, American Brachytherapy Society suggests the tube diameter for brachytherapy should be at least 10 mm. Elekta and Varian have also developed such thickened therapeutic tubes, but the thickened tubes needs to be inserted from the mouth, not from the nasal cavity, and may compress the tumor. Moreover, the tube is inserted into the body cavity guided by a guide wire and an endoscope, and requires the operation by the gastroenterologist. The application of the guide wire increases the operational procedure. Furthermore, placing the tube from mouth will easily induce the vomiting reflex or swallowing reaction, which changes the catheter position and causes discomfort to the patient. Therefore, sedative or anesthesia is needed and the patients must also lie on their side, which increase operational inconvenience and risk. However, after obtaining the tumor imaging data, the doctor will decide the treatment plan of the patient (for determining the position and duration of the radioactive source), and then move the patient to the bed for brachytherapy. At this time, as long as the bent curvature of the patient changes, the applicability of the doctor's treatment plan is reduced, resulting in the treatment being inaccurate.

Multiple balloons catheters further include the catheter disclosed in U.S. Pat. No. 6,527,692B1, which is used for brachytherapy in blood vessels. It also has more than two balloons which can be individually inflated with gas or filled with fluid. The purpose of filling individually is to fix the position of the catheter while allowing the blood to flow through the blood vessel in untreated areas without clogging, since the other unused balloons can be deflated immediately. However, the balloons have donut shape or spiral shape and are added to the catheter externally. It is necessary to fill the balloon with a certain amount of air/liquid for maintaining the supporting function of the shape. Therefore, in the case of a small volume filling, it will likely result in uneven and displacement, and the radioactive source cannot be maintained at the center. However, if the volume is too large for the purpose of maintaining the balloon's donut or spiral shape, in the event that the body cavity is narrow due to excessive tumor growth, this may cause discomfort to the patient or even tumor rupture and bleeding of the tumor. Moreover, during the catheter is inserting into the patient's narrow cavity clinically, even if the balloon externally added to the catheter is in a deflated state, the presence of the external balloon may affect the smoothness of the insertion. When entering the body cavity, it will rub against the patient's body cavity wall and cause discomfort or even damage to the cavity wall.

U.S. Pat. No. 5,910,101 discloses a catheter having more than two balloons which can be individually inflated with gas/filled with fluid. The purpose of having more than two balloons is that brachytherapy can still be administered even at the bend of the blood vessels. However, the dose of radiative source is the most important part of brachytherapy and is inversely proportional to the square of the distance from the radioactive source. Although this catheter makes it possible to apply treatment at a bend due to the multi-balloons design, it still fails to solve the problems of the non-uniform inflation of the balloons while the inflation is insufficient or the adhesion of the balloons on the catheter is offset, resulting in the radioactive source being unable to be maintained in the center of the catheter. A catheter for brachytherapy disclosed in U.S. Pat. No. 7,384,411B1 is also suitable for use in blood vessel brachytherapy. In order to maintain a smooth blood flow, a design of a communication structure is adopted on the catheter. The communication structure provides a channel, so that after the catheter is inserted into the body, the patient's blood and the like can smoothly pass through, avoiding clogging of the vessel. It can also be applied to the treatment of the respiratory tract and allow the passage of air required by the patient. However, when the balloon is used by the catheter, the balloon is added to the periphery of the catheter's communication structure, which increases the volume of the catheter. It may also rub against the body cavity wall when it entering the body cavity, causing discomfort to the patient or even wall injury.

The existing catheters have the above disadvantages. Therefore, designing a catheter which can reduce exposure of the normal tissue to radiation, avoid side effects, while meeting the needs of avoiding multiple operations in the case of multiple tumors or diffuse tumors, avoiding the consumption of large amount of time exhaustion of the patient, without the aid of guide wire, avoiding multiple operations, without relying on externally added balloons or thickened tubes, and avoiding the influence on the smoothness and discomfort while being placed into the patient's narrow cavity, is the actual problem to be solved.

SUMMARY

The present application provides a catheter apparatus, including: a tubular member; multiple fluid-flow pipe members, each having a proximal end and a distal end, and each being disposed along a first axial direction of the tubular member; multiple node members disposed along the axial direction of the tubular member, wherein every two adjacent node members of the multiple node members form a segment; and a periphery member, wherein the multiple node members are wrapped by the periphery member to form a space with the segment formed between the two adjacent node members.

Based on the above concept, wherein the catheter apparatus is provided with multiple periphery members, each of the multiple periphery members wraps the segment formed between the two adjacent node members individually to form a space with the segment formed between the two adjacent node members.

Based on the above concept, wherein a quantity of the fluid-flow pipe members is more than 4; a quantity of the node members is more than 5; and a quantity of the periphery members is more than 4.

Based on the above concept, wherein the multiple fluid-flow pipe members are provided with a control element at the proximal ends, and the control element is configured for individually inflating and deflating the periphery member connected to the distal end of the fluid-flow pipe member at the segment.

Based on the above concept, wherein the multiple fluid-flow pipe members are provided with multiple control elements at the proximal ends, and each of the multiple control elements is disposed individually at the proximal end of the multiple fluid-flow pipe members; each control element is configured for individually inflating the periphery member connected to the distal end of the fluid-flow pipe member at the segment.

Based on the above concept, wherein the node member is a hollow column, a hollow space of the hollow column is configured for the tubular member to pass through the node member along the first axis direction; a channel is disposed on a wall of the hollow column along the first axis direction, and the channel is configured for the fluid-flow pipe member to pass through the node member along the first axis direction.

Based on the above concept, wherein a connecting ring member is further provided outside the hollow column of the node member; the periphery member is connected with the node member by the connecting ring member to form a sealed space by the segment formed between the two adjacent node members.

Based on the above concept, wherein the catheter apparatus is further provided with an outer ring member configured for the periphery member to fasten with the connecting ring member.

Based on the above concept, wherein the node member is a hollow column, a hollow space of the hollow column is configured for the tubular member to pass through the node member along the first axis direction; a channel is disposed on a wall of the hollow column along the first axis direction, and the channel is configured for the fluid-flow pipe member to pass through the node member along the first axis direction; wherein outside of the hollow column of the node member is further provided with a protruding ring member; the multiple periphery members are connected with the protruding ring member of the two adjacent node members along the first axial direction to form a space with the segment formed between the two adjacent node members.

Based on the above concept, wherein lengths of at least two of the fluid-flow pipe members are different, so that the multiple fluid-flow pipe members are connected to the different segments individually.

Based on the above concept, wherein each of the multiple fluid-flow pipe members has an opening, each of the openings is located on the different segments, so that fluid is transferred to the different segments through the opening of fluid-flow pipe member individually.

The present invention also provides a brachytherapy system, comprising: an after-loading treatment instrument; a catheter apparatus based on the above concept connected to the treatment instrument; and a radioactive source, released from the after-loading treatment instrument to the tubular member of the catheter apparatus.

Based on the above concept, the brachytherapy system is further provided with a tumor imaging instrument, wherein the after-loading treatment instrument releases the radioactive source to the segment of the tubular member according to determination by the tumor imaging instrument.

Based on the above concept, wherein the tumor imaging instrument comprises X-ray imaging, fluoroscopy, computed tomography, positron tomography, single photon emission tomography, and nuclear magnetic resonance imaging.

BRIEF DESCRIPTION OF DRAWINGS

FIG. 8(a) is an illustrative diagram of the outer ring member in one embodiment.

FIG. 8(*b*) is an illustrative diagram of the connecting ring member of the node member connected with the outer ring member.

FIG. 8(*c*) is an illustrative diagram of the connecting ring member of the node member connected with the outer ring member.

FIG. 10(*a*) is a three-dimensional illustrative diagram of the node member with the outer ring member in one embodiment.

FIG. 10(*b*) is a front view illustrative diagram of the node member with the outer ring member in one embodiment.

FIG. 10(*c*) is a side view illustrative diagram of the node member with the outer ring member in one embodiment.

DETAILED DESCRIPTION

Unless otherwise defined, all technical and scientific terms in the context represent the same meanings which a person having ordinary skill in the art comprehends with.

The "catheter apparatus" of the present application can be explained according to the following description of the embodiments, which allows one skilled in the art to understand the spirit of creation and make the catheter apparatus.

The modes of implementation of the present application are not limited by the embodiments.

Figure 4:
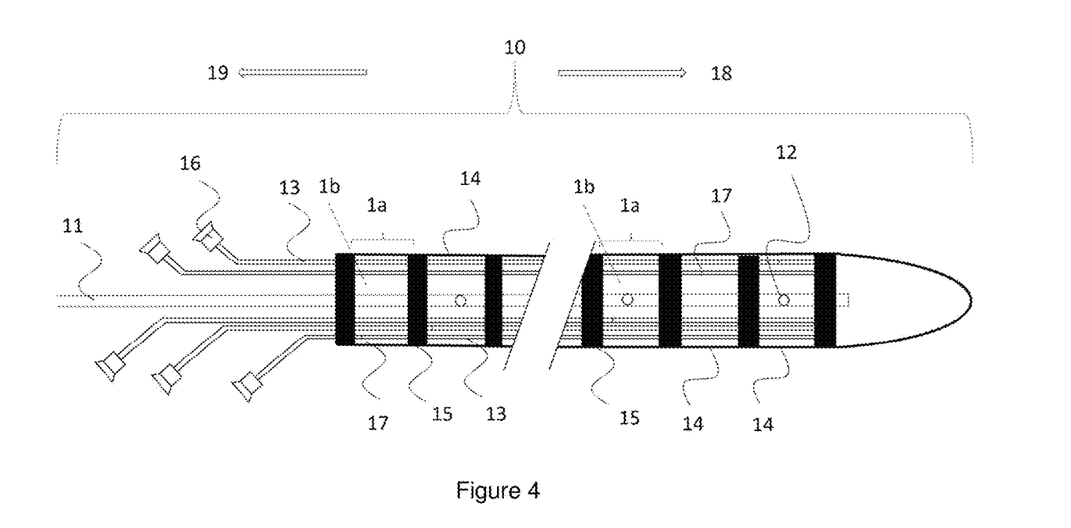
FIG. 4 is an illustrative diagram showing the structure of the catheter apparatus in one embodiment of the present application.

FIG. 4 shows an illustrative diagram of the catheter apparatus 10 in one embodiment of the present application. Within the catheter apparatus, there is a tubular member 11 for placing a radioactive source 12. Multiple fluid-flow pipe members 13 are disposed along a first axial direction of the tubular member 11, wherein the "first axial direction" in the embodiment of the present application is the direction by taking the length of the catheter apparatus as the axis. The catheter apparatus 10 has multiple node members 15, which are disposed along the first axial direction of the tubular member 11, wherein every two adjacent node members 15 form a segment 1*a* therebetween, and each segment 1*a* form a space 1*b* with the periphery member 14. Each of the multiple fluid-flow pipe members 13 has an opening 17 at the distal end 18 and an independent control element 16 at the proximal end 19. The control element can be a medical pump, syringe, or injection device in some embodiments. The control element 16 transfers the fluid into the fluid-flow pipe member 13 to reach the opening 17 (not shown in figures). The fluid appears in the segment 1*a* between the two adjacent node members 15 and fills a space 1*b*, allowing the periphery member 14 to inflate and deflate to achieve the effect of positioning. Because the position of each of the openings 17 is disposed at a different position of the segments 1*a*, this allows different fluid-flow pipe members 13 to transfer the fluid into different segments 1*a* through the openings 17, and allows each of the periphery members 14 to inflate and deflate to achieve individual adjustment of the degree of inflation and deflation.

The tubular member 11, the fluid-flow pipe member 13 and the periphery member 14 are made of soft and bendable materials. The materials can be silicone, latex, plastic as PVC, PU, PP, PE, PTFE or other biocompatible materials or compositions thereof. This allows the periphery member 14 to be inflatable after being filled. The tubular member 11 and the fluid-flow pipe member 13 can be designed to have different length and diameter adapted for different body parts to be treated. The segment 1*a* formed between two adjacent node members 15 may also be designed to have different length according to the needs.

In an embodiment of esophageal cancer, the catheter apparatus 10 can be designed to have a length of 900-1400 mm, preferably a length of 900-1200 mm. The outer diameter of the tubular member 11 can be designed to be 2-6 mm, preferably 5.3 mm; and the inner diameter can be 1-5 mm, preferably 2.0-2.1 mm, so long as a lumencath for assisting the placement of the radioactive source (not shown in figures) is able to be placed therein.

In an embodiment of rectum, the catheter apparatus 10 can be designed to have a length of 300-600 mm, preferably a length of 400-600 mm. The outer diameter of the tubular member 11 can be designed to be 6-15 mm, preferably 10 mm; and the inner diameter can be 1-5 mm, preferably 2.0-2.1 mm, so long as a lumencath for assisting the placement of the radioactive source (not shown in figures) is able to be placed therein.

The fluid-flow pipe member 13 is of the same length as the tubular member 11 in some embodiments, with at least one opening 17 located in a different segment 1*a*. The fluid-flow pipe member 13 may have an inner diameter between 0.2 and 3 mm, preferably an inner diameter of 0.7 mm. In an embodiment for esophageal cancer, the distance between the center of the fluid-flow pipe member 13 and the center of the tubular member is 0.6-3 mm, preferably 1.8-1.9 mm. In an embodiment for rectal cancer, the distance between the center of the fluid-flow pipe member 13 and the center of the tubular member is 2-5 mm, preferably 3.9 mm.

The material of the node member 15 may also be silicone, latex, plastic as PVC, PU, PP, PE, PTFE or other biocompatible materials or compositions thereof. Developing materials such as those having X-ray development lines or barium sulfate may also be further added. In an embodiment of esophageal cancer, the length of the node member 15 may be 1-15 mm, preferably 1-8 mm. In an embodiment of rectal cancer, the length of the node member 15 may be 1-15 mm, preferably 5-15 mm.

In order to achieve complete airtight between the tubular member 11 and the node member 15, between the fluid-flow pipe member 13 and the node member 15, and between the periphery member 14 and the node member 15, so as to allow the periphery member to successfully inflate and deflate, adhesive (not shown in figures) can be used for assistance.

In some embodiments, multiple fluid-flow pipe members 13 may be connected by one single control element (not shown in figures), such as an air inflation apparatus controlled by a computer that is connect to multiple fluid-flow pipe members 13 and independently controls each periphery member 14 connected to the distal end 18 through valve. In an embodiment of esophageal cancer, the periphery member 14 can have a length of 5-20 mm, preferably 16.5 mm, and may expand to a diameter of 30 mm or less. In an embodiment of rectal cancer, the periphery member 14 can have a length of 20-50 mm, preferably 30 mm, and may inflate to a diameter of 50 mm or less.

Figure 5:
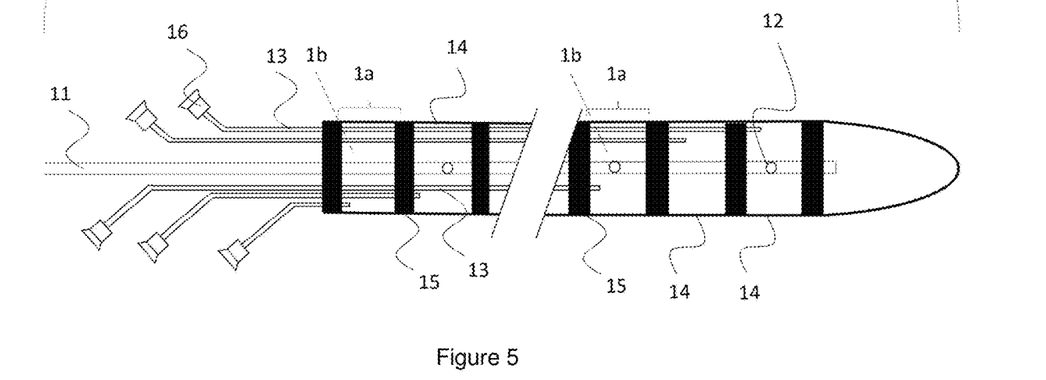
FIG. 5 is an illustrative diagram showing different length of the fluid-flow pipe members in one embodiment of the present application.

FIG. 5 is an illustrative diagram of another embodiment of the catheter apparatus 10 of the present application, wherein the lengths of the fluid-flow pipe members 13 are different from each other, so that different fluid-flow pipe members 13 are individually connected to different segments 1a and fill the spaces 1b, allowing each periphery member 14 to inflate and deflate to achieve individual adjustment of the degree of inflation and deflation.

Figure 6:
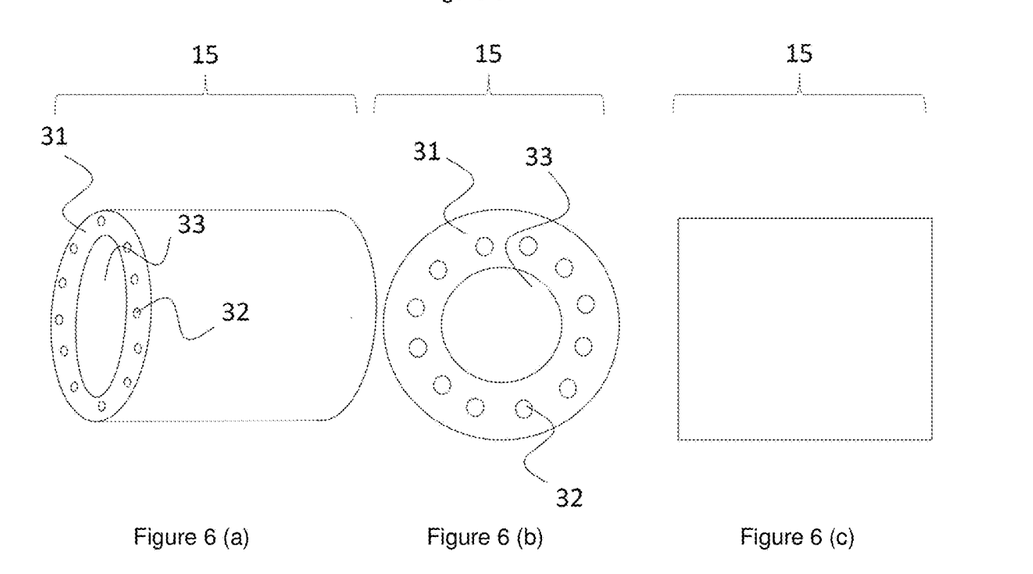
FIG. 6(a) is a three-dimensional illustrative diagram of the node member.
FIG. 6(b) is a front view illustrative diagram of the node member.
FIG. 6(c) is a side view illustrative diagram of the node member.

FIGS. 6(a), 6(b), and 6(c) are three-dimensional, front view and side view illustrative diagrams of the node member 15 of the present application, respectively. Refer to FIG. 2 along with 6(a), 6(b) and 6(c), the node member 15 is a hollow column, wherein the hollow space of the hollow column 33 may allow the tubular member 11 to pass along the hollow space of the hollow column 33 through the node member 15. A channel 32 is disposed on the column wall 31 of the node member 15, so that the fluid-flow pipe member 13 may pass through the node member 15. This allows the space 1b formed between the segment 1a between two adjacent node members 15, and the periphery member 14, to be sealed. That also allows the tubular member 11 and the fluid-flow pipe member 13 to pass through the node member 15 while the periphery member 14 is inflated by being filled with fluid.

Figure 7:
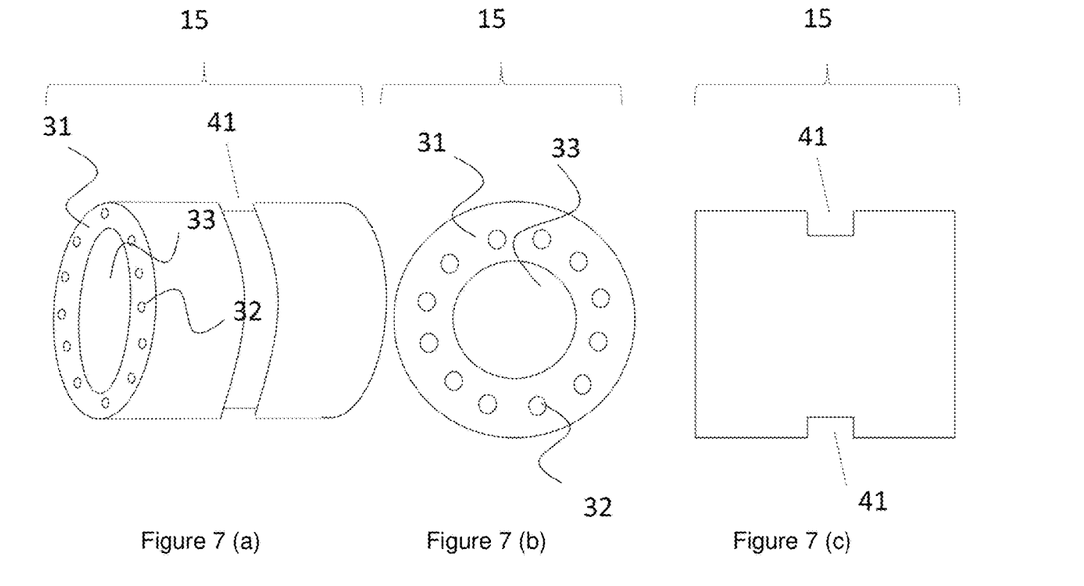
FIG. 7(a) is a three-dimensional illustrative diagram of the node member with the connecting ring member.
FIG. 7(b) is a front view illustrative diagram of the node member with the connecting ring member.
FIG. 7(c) is a side view illustrative diagram of the node member with the connecting ring member.

FIGS. 7(a), 7(b), and 7(c) are three-dimensional, front view and side view illustrative diagrams of the node member 15 with the connecting ring member 41 according to the present application, respectively. FIGS. 8(a), 8(b), and 8(c) are illustrative diagrams of the connecting ring member 41 of the node member connected with the outer ring member 51. In this embodiment, the connecting ring member 41 is a ring-shaped groove which can be combined with the outer ring member 51 of FIG. 8(a), as shown in FIGS. 8(b) and 8(c). In some embodiments, the outer ring member 51 can be rubber band with elastic tightening force, or elastic biocompatible materials, or non-elastic plastic, metal or the like.

Figure 9:
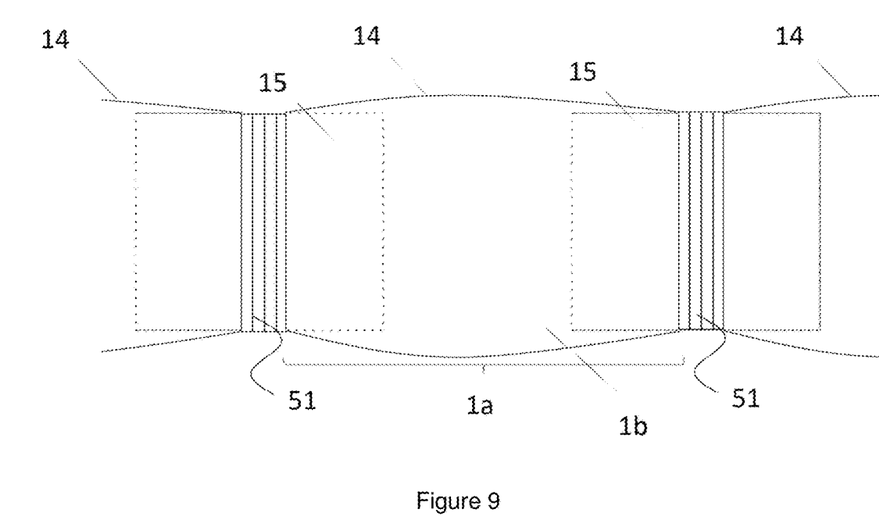
FIG. 9 is an illustrative diagram of the node member connecting with the outer ring member and the periphery member in one embodiment.

FIG. 9 is an illustrative diagram of the node member 15 connecting with the outer ring member 51 and the periphery member 14 in one embodiment. As shown in FIG. 9, the two adjacent node members 15 fix the periphery member 14 by the connecting ring member 41 and the outer ring member 51, and form a space 1b, so that a fluid (not shown in figures) can enter the space 1b and lead to inflation and deflation of the periphery member 14 of the space 1b. In this embodiment, the quantity of the periphery member 14 can be one. Different segments 1a of the periphery member 14 may be inflatable and deflatable individually by pressure segmentation from the outer ring member 51 and the connecting ring member 41 of the node member 15.

Figure 8:
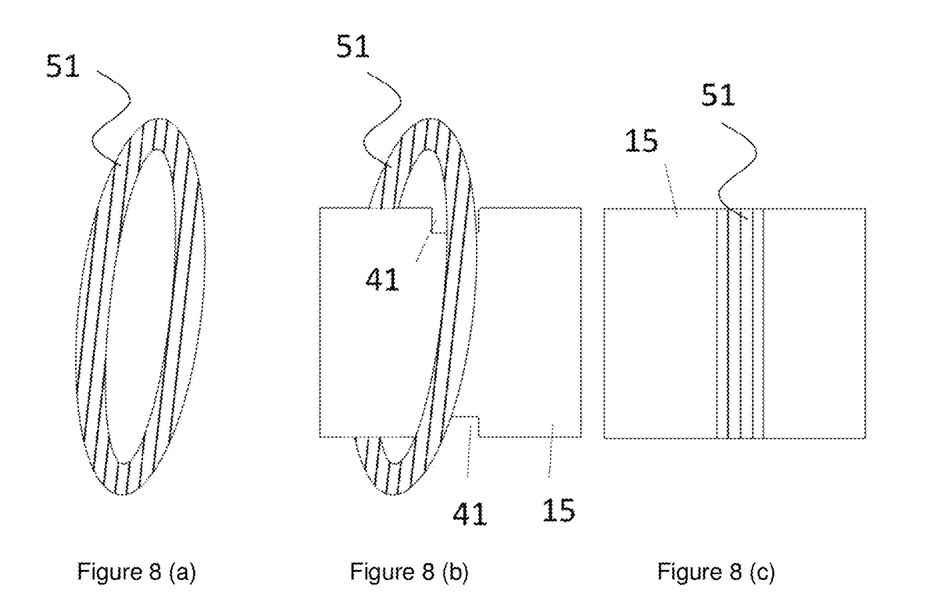
Figure 10:
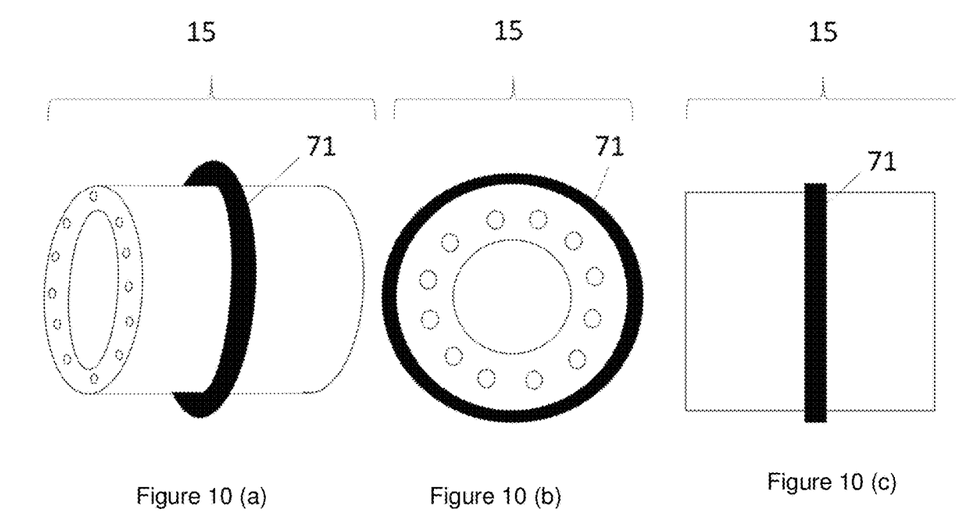
Figure 11:
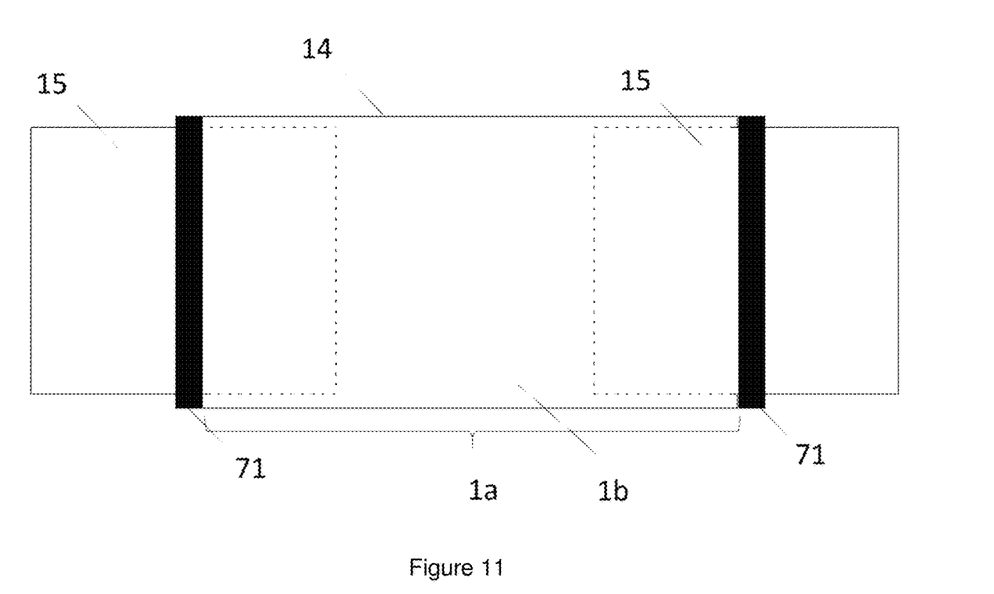
FIG. 11 is an illustrative diagram of the node member with the outer ring member connected with periphery member.

In the embodiment of FIGS. 10 (a)-10(c), the node member 15 has a protruding ring member 71. FIGS. 10(a), 10(b), and 10(c) are three-dimensional, front view and side view illustrative diagrams of the node member 15 with the protruding ring member 71 according to the present application, respectively. FIG. 11 is the illustrative diagram of the periphery member 14 connected with the protruding ring member 71, while the node member 15 having protruding ring member 71. The periphery member 14 is connected to the protruding ring member 71 of the two adjacent node members 15, so that the segment 1a, formed between two adjacent node members 15, forms a sealed space 1b, which allows the periphery member 14 to be inflated or deflated due to the filling of the fluid. In this embodiment, the number of periphery members 14 may be multiple, and may be 4 to 16 as required, connected to the segment formed between different two adjacent node members 15, respectively. FIG. 8 is an illustrative diagram of the periphery member 14 wrapped around the segment 1a as a film, wherein the film thickness of the periphery member 14 is 0.1-2 mm preferably. In an embodiment of esophageal cancer, the periphery member 14 can have a length of 5-50 mm, preferably 5-20 mm. In an embodiment of rectal cancer, the periphery member 14 can have a length of 5-50 mm, preferably 20-50 mm.

Figure 12:
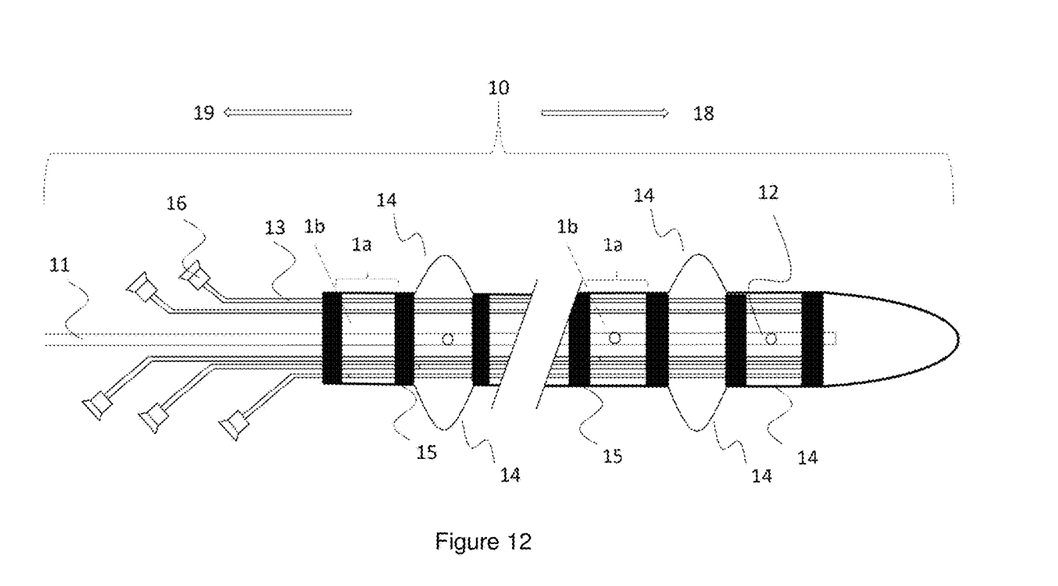
FIG. 12 is an illustrative diagram of the inflated periphery member.

FIG. 12 is an illustrative diagram of the periphery member 14 of the catheter apparatus 10 according to the present application, which may be inflatable and deflatable because of the presence of the node member 15. In the present application, since the different spaces 1b can be individually controlled in terms of whether be filled with the fluid or not and the amount of each filling, the degree of inflation and deflation of each periphery member 14 can be individually controlled. When the size of tumor growth in different segments is different, according to the actual tumor growth situation in the patient's body cavity, the periphery member 14 may be inflated by being filled with a smaller amount of fluid at a narrowing of the body cavity (due to a larger or more protruding tumor), or the periphery member 14 may be inflated to a larger size by being filled with more fluid when the tumor grows more superficially (the esophageal lumen is less narrow), thereby achieving the purpose of killing the tumor with less radiation dose, thereby reducing side effects. Moreover, when the periphery member 14 is attached to the catheter, due to the design of the node member 15, the periphery member 14 can be accurately joined by using an adhesive (not shown in figures). This improves the problem of the presence of radiation hot spots caused by the unevenness of the balloon inflation easily caused by displacement of the attachment site, when external balloons are added to a catheter in the existing technology.

In the present application, due to the design of the periphery member 14 and the node member 15, the effect of inflation can be achieved by only a small amount of inflation. Therefore, when determining the degree of inflation, a smaller amount of inflation can be selected to improve the problem of the shrunk balloon prior to inflation in the existing technology shown in FIG. 3(b), which needs to be filled with a certain amount of fluid for maintaining the shape of the balloon. In the present application, because of the design of the periphery member 14 and the node member 15, it is not necessary to add an external balloon as in the previous technology, which causes rubbing against the wall of the body cavity and discomfort to the patient or even wall damage when the catheter is inserted into the body cavity. That improves the smoothness during placement of the catheter into the narrow cavity of the patient.

Figure 13:
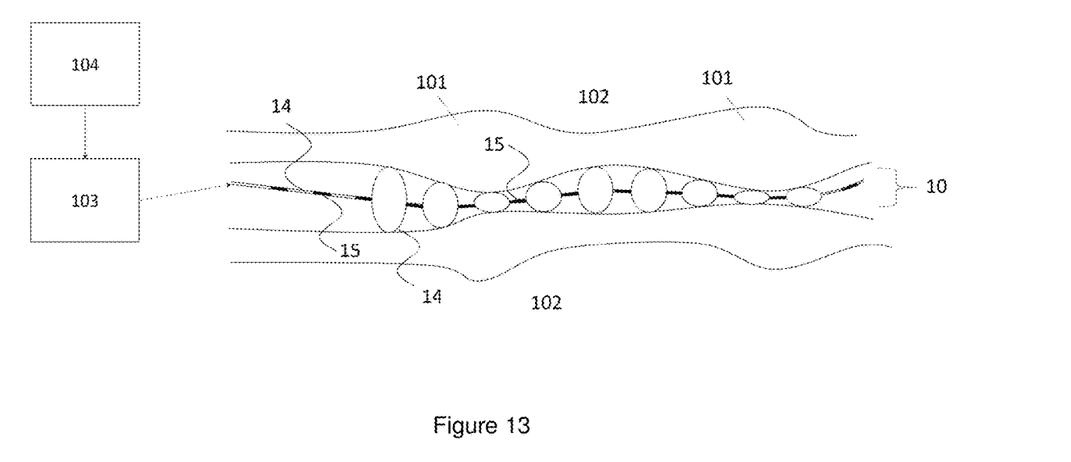
FIG. 13 is an illustrative diagram of each periphery member of the catheter apparatus of the present application inflated and deflated individually for the conformity to the tumor.

FIG. 13 is an illustrative diagram of the periphery members 14 of the catheter apparatus 10 inflatable and deflatable individually to control the sizes thereby conforming to the tumor tissue 101 according to the present application. After being connected to the after-loading medical instrument 103, the catheter apparatus 10 (some of the components are omitted) can determine the position at which the periphery members 14 need to be inflated and deflated, and the range of inflation and deflation, along the volume of the tumor tissue 101 in the lumen. Then, the radioactive source 12 is placed for brachytherapy. Since the periphery members 14 of the catheter apparatus 10 of the present application can be individually inflated and deflated, the catheter apparatus 10 can conform to the shape of the tumor tissue 101. When arranging the treatment plan for the patient, the irradiation area of the tumor tissue 101 may be increased and the irradiation dosage of the normal tissue 102 may be decreased. That increases the cure rate of the patient and reduces side effects.

The position at which the periphery member 14 is inflated and deflated, and the range of the inflation and deflation are determined according to the image taken by the tumor imaging instrument 104. The tumor imaging instrument 104 includes X-ray imaging, fluoroscopy (fluoroscope), computed tomography scan (CT Scan), positron tomography (PET), single photon emission tomography (SPECT), nuclear magnetic resonance imaging (MRI), and the like.

In the past, image positioning used a 2D planar system, taking two images being the front and the side, causing the possibility of the presence of spatial errors. Currently, there has been a tendency to use stereotactic orientation of computed tomography. At this time, the fixation effect of the catheter apparatus 10 in the lumen is very important. Since the catheter apparatus 10 conforms to the shape of the tumor tissue 101, the catheter apparatus 10 and the tumor tissue 101 have an effect of closely fitting to each other, and have a good fixation effect, allowing the treatment plan to be more precise. This successfully solves the problems of lowered accuracy of treatment plan caused by the movement of the catheter apparatus 10 due to the patient's breath or the movement during the processes of tumor imaging and the placement of the radiation source.

In summary, compared with the known technology, for example, Bonvoisin-Gerard Esophageal Applicator and Standard Nasopharyngeal Applicator Set of Elekta, and the catheters disclosed in U.S. Pat. Nos. 7,384,411B1, 6,575,932B1, Chinese Patent Publication No. 202387089U, U.S. Pat. Nos. 6,527,692 B1 and 5,910,101, etc., the present application increases the fixation effect, reduces the radiation area of normal tissues, and reduces side effects. At the same time, since the periphery member 14 is segmented by the outer ring member 51 and the connecting ring member 41 of the node member 15, or is segmented in a manner of multiple periphery members 14, Different segments 1a of the periphery member 14 can be inflated and deflated individually, for example having 4-16 individually inflatable and deflatable periphery members 14. In the case of multiple tumors or diffuse tumors, the present application can be fixed wherever necessary, and relies solely on moving the radioactive source to treat multiple diffuse cancer areas without repeated operations, consuming a large amount of time or exhausting the patient. Since the degree of inflation and deflation and the size of the periphery member 14 can be individually controlled, the degree of inflation and deflation and the size of each periphery member 14 can be determined according to the tumor condition during use, thereby fixing according to the shape of the entire segment of the tumor. Thus, even if displacement occurs when the patient breathes or moves, the catheter apparatus 10 has already been conformed to and fixed the tumor, and can move along with the tumor tissue without sliding. This will not lead to change of position relative to the tumor tissue and increases the accuracy of the physician's treatment plan.

The technical features of the present invention can be utilized in any catheter treatment which needs to keep the body cavity open. Hereinafter, the treatment of esophageal cancer and rectal cancer will be exemplified, and the application steps will be described to assist a person having ordinary skill in the art to understand the possible application of the present invention. The invention may be applied in place of other steps of use without departing from the scope of the present application:

Esophageal Cancer:

The catheter apparatus 10 is placed into the esophagus from the nasal cavity. In the state in which the periphery member 14 has not been inflated and deflated, the catheter apparatus 10 can be smoothly placed into the esophagus from the nasal cavity without interference from the external balloon, so that it is not necessary to be placed from the oral cavity. After the catheter apparatus 10 is placed in the esophagus, it is fixed to the outside of the nostrils by adhesion with a tape.

A lumen cath (not shown) is placed in the tubular member 11 of the catheter apparatus 10 until the end, and the lumen cath (not shown) is fixed to the tubular member 11 by adhesion with a tape.

The open end of the lumen cath (not shown) is then connected to the after-loading treatment instrument 103 and a simulated radioactive source that can measure the relative depth of the lumen and develop a CT image is placed therein.

The scout view image (reconstructed planar image) of that portion of the patient is obtained, the distribution area of the simulated source is observed, and the tumor area of the computerized tomographic reconstructed planar image of the treatment planning system is compared to determine the position and degree of inflation of the periphery member 14 which inflates relative to the catheter apparatus 10. Because the catheter apparatus 10 of the present application has a sufficient number of periphery members 14 (e.g. 8 inflatable and deflatable periphery members), even if it is a diffuse tumor, no movement is required after the catheter apparatus is placed, which makes the patient comfortable without anesthesia.

After inflating some of the periphery members 14, the computer tomographic image is scanned to confirm that the inflated size is appropriate. If necessary, the size is adjusted and a computerized tomographic image is rescanned after modification.

The computed tomography image is transmitted to the treatment planning system, depicting the location and area of the tumor when the periphery member 14 is inflated, as well as depicting the surrounding normal tissue (e.g. lung, heart, spinal cord, etc.).

A 3D treatment plan (dose calculation) is made for the patient's various tumor size and shape to ensure that the tumor area is adequately dosed and that the receiving dose of the normal tissue is within a safe range.

The treatment is performed and the irradiation is administrated.

Rectal Cancer:

The catheter apparatus 10 is placed from the anus of the patient to the rectum, and the catheter apparatus 10 is fixed to the outside of the anus by adhesion with a tape.

A lumen cath (not shown) is placed in the tubular member 11 of the catheter apparatus 10 until the end, and a lumen cath (not shown) is fixed to the tubular member 11 by adhesion with a tape.

The open end of the lumen cath (not shown) is then connected to the after-loading treatment instrument 103 and a simulated radioactive source that can measure the relative depth of the lumen and can develop a CT image is placed therein.

The scout view image (reconstructed planar image) of that portion of the patient is obtained, the distribution area of the simulated source is observed, and the tumor area of the computerized tomographic reconstructed planar image of the treatment planning system is compared to determine the position and degree of inflation of the periphery member 14 which inflates relative to the catheter apparatus 10. Because the catheter apparatus 10 of the present application has a sufficient number of periphery members 14 (e.g. 8 inflatable and deflatable periphery members), even if it is a diffuse tumor, no movement is required after the catheter apparatus is placed, which makes the patient comfortable without anesthesia.

After inflating some of the periphery members 14, the computer tomographic image is scanned to confirm that the inflated size is appropriate. If necessary, the size is adjusted and the computerized tomographic image is rescanned after modification.

The computed tomography image is transmitted to the treatment planning system, depicting the location and area of the tumor when the periphery member 14 is inflated, as well as depicting the surrounding normal tissue (e.g. uterus and ovaries in female; prostate, bladder, etc. in male).

A 3D treatment plan (dose calculation) is made for the patient's various tumor size and shape to ensure that the tumor area is adequately dosed and that the receiving dose of the normal tissue is within a safe range.

The treatment is performed and the irradiation is administered.

The present invention does not require the aid of the guide wire, can irradiate the entire diffuse tumor in one brachytherapy without placing the catheter and the radioactive source repeatedly, and can avoid changes of the relative position between the catheter and the tumor that is caused by the breathing or movement of the patient which affects the accuracy of the treatment plan. The present application does not need to be placed from the oral cavity for the treatment of esophageal cancer, and it is not necessary to administer anesthesia to the patient. In addition, instead of an external balloon, inflatable and deflatable components such as the periphery member 14 and the node member 15 are provided to achieve the therapeutic purposes. There is no external balloon that generally rubs against the body cavity wall when it entering the body cavity which causes discomfort to the patient or even wall damage. It greatly improves the smoothness when being placed into a narrow cavity of the patient, solving the problems of the existing technology and achieves a better effect.

SYMBOL DESCRIPTION

Catheter apparatus 10
Tubular member 11
Radioactive source 12
Fluid-flow pipe member 13
Periphery member 14
Node member 15
Control element 16
Opening 17
Distal end 18
Proximal end 19
Segment 1a
Space 1b
Column wall 31
Channel 32
Hollow space of the hollow column 33
Connecting ring member 41
Outer ring member 51
Protruding ring member 71
Tumor tissue 101
Normal tissue 102
After-loading treatment instrument 103
Tumor imaging instrument 104
Gross tumor volume GTV
Clinical target volume CTV
Internal target volume ITV
Planning target volume PTV

The invention claimed is:

1. A catheter apparatus, comprising:
a tubular member;
multiple fluid-flow pipe members disposed along a first axial direction of the tubular member, wherein each of the fluid-flow pipe members has a proximal end and a distal end;
one or more periphery members; and
multiple node members disposed along the first axial direction of the tubular member,
wherein the multiple node members are wrapped by the one or more periphery members to form a sealed space between every two adjacent node members of the multiple node members,
wherein every two adjacent node members of the multiple node members are not in direct contact with each other and form a segment within the sealed space,
wherein each of the multiple node members is a hollow column having a hollow space configured for the tubular member to pass through the hollow column along the first axial direction, and
wherein a wall of the hollow column has multiple channels disposed thereon along the first axial direction and configured for the multiple fluid-flow pipe members to pass through the hollow column along the first axial direction.

2. The catheter apparatus according to claim 1, wherein the quantity of the periphery members is more than 1.

3. The catheter apparatus according to claim 2, wherein a quantity of the fluid-flow pipe members is more than 4; a quantity of the node members is more than 5; and a quantity of the periphery members is more than 4.

4. The catheter apparatus according to claim 1 or 2, wherein all of the proximal ends of the multiple fluid-flow pipe members are connected to one control element, and the control element is configured for individually inflating or deflating each of the periphery members.

5. The catheter apparatus according to claim 1 or 2, wherein each of the multiple fluid-flow pipe members has a control element at the proximal end thereof, and the control element is configured for individually inflating or deflating each of the periphery members.

6. The catheter apparatus according to claim 1, further comprising a connecting ring member provided outside each of the multiple node members, and each of the periphery members is connected with every two adjacent node members of the multiple node members by the connecting ring member to form the sealed space.

7. The catheter apparatus according to claim 6, further comprising an outer ring member configured for each of the periphery members to fasten with the connecting ring member.

8. The catheter apparatus according to claim 1, wherein each of the multiple node members has a protruding ring member provided outside thereof.

9. The catheter apparatus according to claim 1, wherein at least two of the fluid-flow pipe members have different lengths.

10. The catheter apparatus according to claim 1, wherein each of the multiple fluid-flow pipe members has an opening individually.

11. A brachytherapy system, comprising:
- a tumor imaging instrument comprising X-ray imaging, fluoroscopy, computed tomography, positron tomography, single photon emission tomography, or nuclear magnetic resonance imaging;
- an after-loading treatment instrument;
- a catheter apparatus according to claim 1 connected to the after-loading treatment instrument; and
- one or more radioactive sources released from the after-loading treatment instrument to the tubular member within the segment according to a determination by the tumor imaging instrument.

* * * * *